US012558181B2

(12) United States Patent
Verner et al.

(10) Patent No.: US 12,558,181 B2
(45) Date of Patent: Feb. 24, 2026

(54) STAGED FORCE FEEDBACK TRANSITIONING BETWEEN CONTROL STATES

(71) Applicant: Intuitive Surgical Operations, Inc., Sunnyvale, CA (US)

(72) Inventors: Lawton N. Verner, Saratoga, CA (US); Hsien-Hsin Liao, Los Altos, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 287 days.

(21) Appl. No.: 18/204,090

(22) Filed: May 31, 2023

(65) Prior Publication Data

US 2023/0320802 A1      Oct. 12, 2023

Related U.S. Application Data

(60) Division of application No. 17/735,664, filed on May 3, 2022, now Pat. No. 11,701,194, which is a continuation of application No. 16/069,800, filed as application No. PCT/US2017/013237 on Jan. 12, 2017, now Pat. No. 11,357,587.

(60) Provisional application No. 62/277,820, filed on Jan. 12, 2016.

(51) Int. Cl.
A61B 34/00      (2016.01)
A61B 34/30      (2016.01)
A61B 1/045      (2006.01)
A61B 17/00      (2006.01)

(52) U.S. Cl.
CPC .............. *A61B 34/76* (2016.02); *A61B 34/30* (2016.02); *A61B 34/77* (2016.02); *A61B 1/045* (2013.01); *A61B 2017/00199* (2013.01); *A61B 2017/00225* (2013.01)

(58) Field of Classification Search
CPC .......... A61B 1/045; A61B 2017/00199; A61B 2017/00225; A61B 34/76; A61B 34/30; A61B 34/77
See application file for complete search history.

(56) References Cited

U.S. PATENT DOCUMENTS

| 4,160,508 A | 7/1979 | Frosch et al. |
| 4,604,016 A | 8/1986 | Joyce |
| 5,116,180 A | 5/1992 | Fung et al. |
| 5,696,837 A | 12/1997 | Green |
| 5,710,870 A | 1/1998 | Ohm et al. |

(Continued)

FOREIGN PATENT DOCUMENTS

| CN | 102046235 A | 5/2011 |
| CN | 103203755 A | 7/2013 |

(Continued)

OTHER PUBLICATIONS

Office Action for JP Application No. JP2023005621, mailed Oct. 15, 2024, 10 pages.

(Continued)

*Primary Examiner* — Michael J Lau

(57)      ABSTRACT

A surgical system is provided comprising: an input device; and a controller for receiving control inputs from the input device and for providing haptic feedback at the input device, the controller configured to apply a staged transition from a first haptic feedback profile at the input device to a second haptic feedback profile at the input device.

12 Claims, 5 Drawing Sheets

(56) References Cited

U.S. PATENT DOCUMENTS

| | | | |
|---|---|---|---|
| 5,767,648 | A | 6/1998 | Morel et al. |
| 6,024,576 | A | 2/2000 | Bevirt et al. |
| 6,102,850 | A | 8/2000 | Wang et al. |
| 6,377,011 | B1 | 4/2002 | Ben-Ur |
| 6,459,926 | B1 | 10/2002 | Nowlin et al. |
| 6,594,552 | B1 | 7/2003 | Nowlin et al. |
| 6,639,581 | B1 | 10/2003 | Moore et al. |
| 6,723,106 | B1 | 4/2004 | Charles et al. |
| 6,994,703 | B2 | 2/2006 | Wang et al. |
| 7,155,315 | B2 | 12/2006 | Niemeyer et al. |
| 7,248,944 | B2 | 7/2007 | Green |
| 7,373,219 | B2 | 5/2008 | Nowlin et al. |
| 7,843,158 | B2 | 11/2010 | Prisco |
| 7,963,288 | B2 | 6/2011 | Rosenberg et al. |
| 8,041,459 | B2 | 10/2011 | Sutherland et al. |
| 8,170,717 | B2 | 5/2012 | Sutherland et al. |
| 8,343,171 | B2 | 1/2013 | Farritor et al. |
| 8,396,598 | B2 | 3/2013 | Sutherland et al. |
| 8,644,988 | B2 | 2/2014 | Prisco et al. |
| 9,002,518 | B2 | 4/2015 | Manzo et al. |
| 9,014,856 | B2 | 4/2015 | Manzo et al. |
| 9,050,120 | B2 | 6/2015 | Swarup et al. |
| 9,198,714 | B2 | 12/2015 | Worrell et al. |
| 9,220,567 | B2 | 12/2015 | Sutherland et al. |
| 9,339,343 | B2 | 5/2016 | Swarup et al. |
| 9,492,927 | B2 | 11/2016 | Diolaiti et al. |
| 9,649,174 | B2 | 5/2017 | Swarup et al. |
| 11,357,587 | B2 * | 6/2022 | Verner ................... A61B 34/77 |
| 11,701,194 | B2 * | 7/2023 | Verner ................... A61B 34/35 |
| | | | 606/1 |
| 2001/0018591 | A1 | 8/2001 | Brock et al. |
| 2003/0004610 | A1 | 1/2003 | Niemeyer et al. |
| 2003/0060927 | A1 | 3/2003 | Gerbi et al. |
| 2004/0039485 | A1 | 2/2004 | Niemeyer et al. |
| 2004/0106916 | A1 | 6/2004 | Quaid et al. |
| 2004/0243147 | A1 * | 12/2004 | Lipow ................... A61B 34/74 |
| | | | 606/130 |
| 2005/0024331 | A1 | 2/2005 | Berkley et al. |
| 2005/0219206 | A1 | 10/2005 | Schena et al. |
| 2006/0149418 | A1 | 7/2006 | Anvari |
| 2006/0207978 | A1 | 9/2006 | Rizun et al. |
| 2007/0103437 | A1 | 5/2007 | Rosenberg |
| 2007/0142968 | A1 | 6/2007 | Prisco et al. |
| 2007/0239028 | A1 | 10/2007 | Houser et al. |
| 2008/0150891 | A1 | 6/2008 | Berkley et al. |
| 2009/0062813 | A1 | 3/2009 | Prisco et al. |
| 2009/0157059 | A1 * | 6/2009 | Allen ................... A61B 34/25 |
| | | | 606/1 |
| 2009/0195538 | A1 | 8/2009 | Ryu et al. |
| 2009/0228145 | A1 | 9/2009 | Hodgson et al. |
| 2010/0041991 | A1 | 2/2010 | Roundhill |
| 2010/0073150 | A1 | 3/2010 | Olson et al. |
| 2010/0179423 | A1 | 7/2010 | Ramstein et al. |
| 2010/0256558 | A1 | 10/2010 | Olson et al. |
| 2010/0274087 | A1 | 10/2010 | Diolaiti et al. |
| 2011/0071543 | A1 | 3/2011 | Prisco et al. |
| 2011/0082468 | A1 * | 4/2011 | Hagag ................ A61B 17/1684 |
| | | | 606/130 |
| 2011/0118748 | A1 | 5/2011 | Itkowitz |
| 2011/0121953 | A1 | 5/2011 | Grant et al. |
| 2011/0295247 | A1 | 12/2011 | Schlesinger et al. |
| 2011/0295268 | A1 | 12/2011 | Roelle et al. |
| 2012/0116391 | A1 | 5/2012 | Houser et al. |
| 2012/0138658 | A1 | 6/2012 | Ullrich et al. |
| 2012/0143182 | A1 | 6/2012 | Ullrich et al. |
| 2012/0265051 | A1 | 10/2012 | Fischer et al. |
| 2013/0023917 | A1 | 1/2013 | Cruz Hernandez et al. |
| 2013/0053648 | A1 | 2/2013 | Abovitz et al. |
| 2013/0103050 | A1 | 4/2013 | Richmond et al. |
| 2013/0131867 | A1 | 5/2013 | Olds et al. |
| 2013/0169412 | A1 | 7/2013 | Roth |
| 2013/0172906 | A1 | 7/2013 | Olson et al. |
| 2013/0211590 | A1 | 8/2013 | Diolaiti et al. |
| 2013/0274712 | A1 | 10/2013 | Schecter |
| 2013/0289767 | A1 | 10/2013 | Lim et al. |
| 2013/0296737 | A1 | 11/2013 | McMillan et al. |
| 2013/0321262 | A1 | 12/2013 | Schecter et al. |
| 2014/0142582 | A1 | 5/2014 | Biedermann et al. |
| 2014/0142592 | A1 * | 5/2014 | Moon ................... A61B 34/37 |
| | | | 901/8 |
| 2014/0276938 | A1 * | 9/2014 | Hsu ........................ A61B 34/30 |
| | | | 606/130 |
| 2014/0277017 | A1 * | 9/2014 | Leimbach .............. A61B 17/32 |
| | | | 227/175.3 |
| 2014/0330073 | A1 | 11/2014 | Ko et al. |
| 2015/0073340 | A1 | 3/2015 | Pacheco et al. |
| 2015/0119637 | A1 | 4/2015 | Alvarez et al. |
| 2015/0130599 | A1 | 5/2015 | Berkley et al. |
| 2015/0360365 | A1 | 12/2015 | Fudaba et al. |
| 2019/0201137 | A1 | 7/2019 | Shelton, IV et al. |
| 2020/0352665 | A1 | 11/2020 | Itotani et al. |
| 2021/0038334 | A1 | 2/2021 | Hsu et al. |
| 2021/0093409 | A1 | 4/2021 | Overmyer et al. |
| 2022/0331039 | A1 | 10/2022 | Verner et al. |
| 2024/0307139 | A1 | 9/2024 | Kadokura |
| 2024/0398497 | A1 | 12/2024 | Verner et al. |

FOREIGN PATENT DOCUMENTS

| | | | | | |
|---|---|---|---|---|---|
| EP | 2023844 | A2 | 2/2009 | | |
| EP | 2764842 | A1 | 8/2014 | | |
| EP | 3834765 | B1 | 7/2024 | | |
| JP | 2009187550 | A | 8/2009 | | |
| JP | 2010524548 | A | 7/2010 | | |
| JP | 2011519286 | A | 7/2011 | | |
| KR | 20140065895 | A * | 5/2014 | ............. A61B 34/77 |
| KR | 20150007020 | A | 1/2015 | | |
| WO | WO-2005039835 | A1 * | 5/2005 | ............. A61B 34/76 |
| WO | WO-2005074435 | A2 | 8/2005 | | |
| WO | WO-2013059643 | A1 | 4/2013 | | |
| WO | WO-2013169303 | A1 | 11/2013 | | |
| WO | WO-2015148293 | A1 | 10/2015 | | |
| WO | WO-2016201303 | A1 | 12/2016 | | |
| WO | WO-2017123796 | A1 | 7/2017 | | |
| WO | WO-2017146890 | A1 | 8/2017 | | |
| WO | WO-2021211225 | A1 | 10/2021 | | |
| WO | WO-2022193889 | A1 | 9/2022 | | |
| WO | WO-2023076468 | A1 * | 5/2023 | ............. A61B 34/35 |
| WO | WO-2023180891 | A1 | 9/2023 | | |

OTHER PUBLICATIONS

Office Action for KR Application No. 10-2018-7019556, mailed Aug. 22, 2023, 09 pages.

Office Action for CN Application No. 2022100970110, mailed Nov. 22, 2023, 12 pages.

Extended European Search Report for Application No. EP21153585.1 mailed on May 19, 2021, 11 pages.

Extended European Search Report for Application No. 17738963.2 mailed on Aug. 13, 2019, 10 pages.

International Search Report and Written Opinion for Application No. PCT/US2017/013237, mailed on May 2, 2017, 12 pages.

Notice of Allowance for U.S. Appl. No. 17/735,664, mailed Mar. 29, 2023, 8 pages.

Office Action for JP Application No. 2018-533730, mailed Apr. 12, 2022, 15 pages.

Office Action for JP Application No. 2018-533730, mailed Oct. 4, 2022, 20 pages.

Okamura A.M., "Haptic Feedback in Robot-Assisted Minimally Invasive Surgery," Current Opinion in Urology, Jun. 24, 2009, National Institute of Health Public Access, vol. 19 (1), 10 pages.

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

Extended European Search Report for Application No. EP24183856. 4, mailed on Aug. 5, 2024, 10 pages.

Garcia J.G., et al., "Force and Acceleration Sensor Fusion for Compliant Robot Motion Control," Proceedings of the 2005 IEEE International Conference on Robotics and Automation, Apr. 2005, pp. 2709-2714.

(56) References Cited

OTHER PUBLICATIONS

Office Action for CN Application No. 2022100970110, mailed Jun. 27, 2024, 09 pages.
Office Action for JP Application No. JP2018533730, mailed Feb. 20, 2024, 06 pages.
Office Action for JP Application No. JP2023005621, mailed Apr. 9, 2024, 24 pages.
Office Action for KR Application No. KR1020187019556, mailed Feb. 26, 2024, 05 pages.

* cited by examiner

Example Staged Transition Profiles

STAGED FORCE FEEDBACK TRANSITIONING BETWEEN CONTROL STATES

CROSS-REFERENCE TO RELATED APPLICATIONS

This application is a divisional of U.S. application Ser. No. 17/735,664, filed on May 3, 2022, which is a continuation of U.S. application Ser. No. 16/069,800, now U.S. Pat. No. 11,357,587, filed on Jul. 12, 2018, which is a U.S. National Stage Filing under 35 U.S.C 371 from International Application No. PCT/US2017/013237, filed on Jan. 12, 2017, and published as WO 2017/123769 A1 on Jul. 20, 2017, which claims the benefit of priority to U.S. Provisional Patent Application No. 62/277,820, filed on Jan. 12, 2016, each of which is hereby incorporated by reference herein in its entirety.

FIELD

The present invention is directed towards systems and methods for providing haptic feedback to the operator of a surgical system, and more particularly to maintaining an intuitive haptic profile for the user when the control state of the system changes.

BACKGROUND

Tele-operated surgical systems are often intended to enhance surgeon precision and/or reduce patient trauma during a medical procedure. In such systems, a surgeon interacts with input devices (sometimes referred to as "masters" or "master controllers") to control surgical instruments that are actuated by drive mechanisms such as motors. Because the surgeon is not directly manipulating the surgical instruments, it can sometimes be beneficial to provide haptic feedback at the input devices that indicates or replicates the forces felt at the surgical instruments. To provide a good user experience, the surgeon would ideally experience a seamless haptic experience through system state and configuration changes. However, this can be difficult to accomplish, particularly when a given input device is used in multiple different control states. For example, a single input device may be used to control multiple different instruments (requiring switching control between those different instruments), may be used to control an overall positioning of the surgical system (e.g., changing the viewpoint of an endoscope looking at the anatomical region of interest), may be used to change settings of the surgical system, and/or may be simply be disassociated from any control effects.

Simply activating/deactivating/changing haptic feedback in response to such control state changes can create jerky and unintuitive interactions. If a force is being applied to a user in one state and will not be applied to the user in the next state, immediately changing the force from full force on to no force is disconcerting to the user. For example, when transitioning from controlling an instrument with haptic feedback to controlling an instrument without haptic feedback (e.g., the endoscope) or otherwise entering a control state without haptic feedback (or even a different haptic feedback), such as instrument changes (i.e., removal of an instrument from a manipulator), exit from following (i.e., disabling the control of the instrument by the input device), or arm swap (i.e., changing the surgical instrument/arm/ manipulator under control by the input device), an immediate loss of haptic feedback would feel like an unexpected loss of resistance to the user.

Users find it similarly disconcerting if force feedback is immediately enabled when a user transitions from an instrument that is rendering no (or low) force to an instrument with a (high) force. This can happen, for example, when we transition from camera control back to an instrument with force feedback. This also occurs any time a user initially takes control of an instrument (e.g. transitioning first going into following with an instrument).

Another problem arises when the user is changing control states to an intermediate state in which they remain associated with a particular instrument (e.g. clutching, head-in UI, etc.) but control is not being applied. Turning the force feedback off during the intermediate state and back on again when returning to directly controlling the instrument is not ideal for users. Often these intermediate control states are short in duration, so turning on/off the force quickly can be problematic.

Note that the force feedback being presented to the user may be the sum of the feedback from a sensor, from an algorithm, from a user interface cue, collision detection, etc.

SUMMARY

To mitigate the discomfort of abrupt force transitions when changing control states, a staged transition can be performed from the original force being displayed at the input device (and hence, to the user) to a level appropriate for the new control state.

In some embodiments, the haptic feedback force vector transitions (over some non-zero time, in direction and/or magnitude) from force A to force B. Force A magnitude can be greater than or less than force B (or in some embodiments equivalent, where the transition is one of direction only). The profile of the staged transition from the magnitudes of force A to force B can be any profile that takes place over time, including linear or curvilinear transitions, and can include discontinuities (e.g., steps) as part of the transition.

In some embodiments, for the control state changes that involve going into an intermediate mode where the user remains associated with a particular instrument, the force feedback can remain at the level it was last at when the user stopping directly controlling the instrument. For example, if the control state transitions from instrument control (following) to non-instrument control (exit following), the haptic feedback at the associated input device can be maintained at its current level for at least some period of time. In various embodiments, after such stable period, a staged transition to a reduced force or no-force state could subsequently be applied.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

In the following detailed description of the aspects of the invention, numerous specific details are set forth in order to provide a thorough understanding of the disclosed embodiments. However, it will be obvious to one skilled in the art that the embodiments of this disclosure may be practiced without these specific details. In other instances well known methods, procedures, components, and circuits have not been described in detail so as not to unnecessarily obscure aspects of the embodiments of the invention. And, to avoid needless descriptive repetition, one or more components or actions described in accordance with one illustrative embodiment can be used or omitted as applicable from other illustrative embodiments.

By providing a staged transition between force feedback profiles when the control state of a surgical system changes, an intuitive haptic experience can be maintained for the user of the surgical system.

Figure 1B:
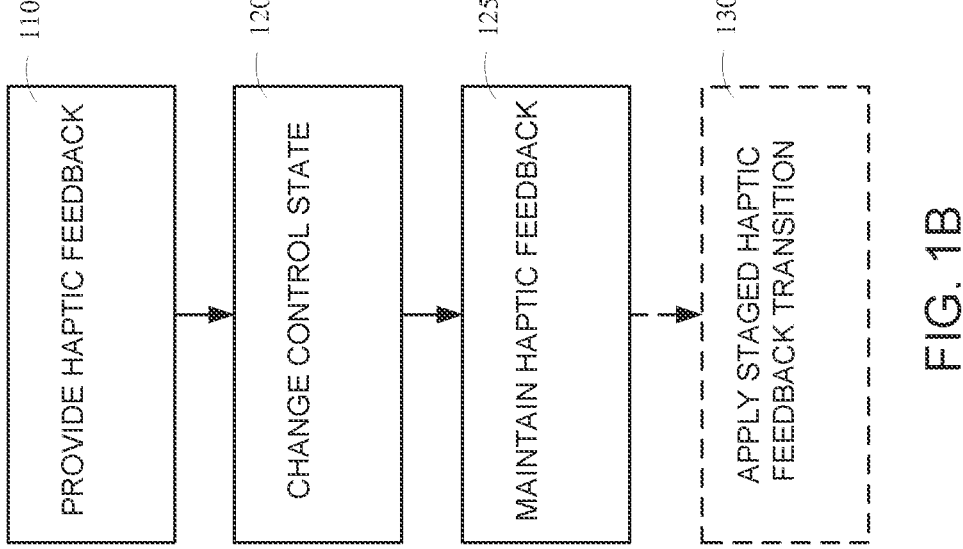
FIGS. 1A-1B show methods of providing intuitive haptic feedback to a user of a surgical system during control state changes, in accordance with various embodiments of the invention.
Figure 1A:
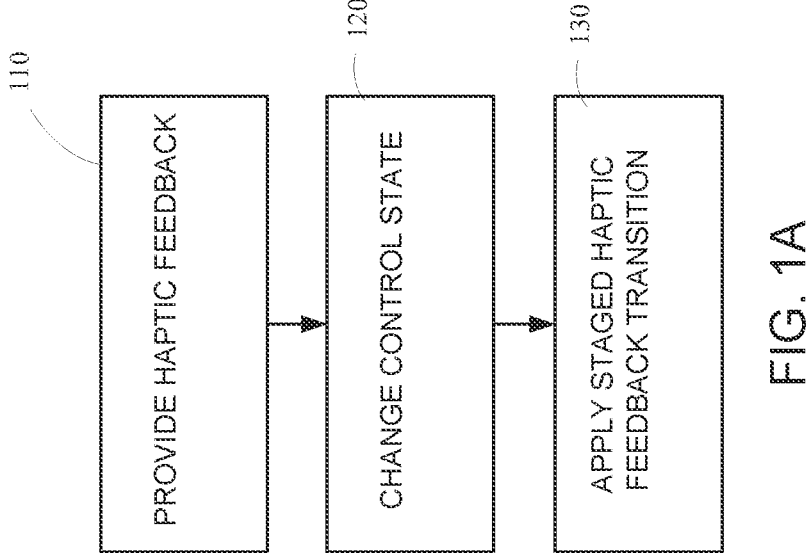

FIG. 1A shows an exemplary method for providing such a staged haptic transition. In a PROVIDE HAPTIC FEEDBACK step 110, a surgical system that allows a user (e.g., surgeon) to control a surgical instrument (and/or other elements of the surgical system, such as a robotic arm, set up structure, or positioning element such as a boom or cart) via an input device(s) (e.g., lever(s), gripper(s), joystick(s), and/or any other structure capable of receiving user input) and then provides force feedback to that input device based on a desired haptic feedback profile (a set of one or more haptic feedback effects that at least partially reproduce or represent the physical experience of a real or virtual/modeled interaction). The haptic feedback profile can be based on any haptic model input, such as sensed forces at the instrument (e.g., tissue or other instrument interactions) or robotic arm (e.g., arm collisions with structures or staff), user guidance (e.g., haptic detents, fences, or other profiles to provide guidance for the user to move the input device(s) along a desired path or trajectory), and user interface (UI) elements (e.g., presenting a virtual handle or steering wheel to the user). The transformation applied to the desired haptic feedback profile to generate the haptic feedback at the input device can be anything from direct replication of the haptic feedback profile, to scaling of the haptic feedback profile, to applying a non-linear modification of the haptic feedback profile, or any other transformation (e.g., force scaling that varies depending on one or more other factors such as instrument state/speed, viewing magnification, etc.). The haptic feedback in step 110 may also include forces that are computed based on additional sensors of the surgical system such as position sensors, buttons, or contact sensors.

Then in a CHANGE CONTROL STATE step 120, a control state change in the surgical system occurs (typically in response to user command/action, but in other examples in response to external commands such as system timer or warning, or third-party action/command), such that inputs at the input device are no longer providing the same effect at the surgical instrument. For example, in a surgical system that includes both a surgical instrument and a camera (e.g., endoscope), there can be instances where the control state changes from one in which the input device is controlling the surgical instrument, to a "camera control mode" where the input device is controlling the viewpoint of the camera/field of view of the surgical site. If the input device is providing haptic feedback to the user when such a control state change occurs, then immediately removing the haptic feedback in response to the change would result in an abrupt loss of force feedback at the input device, which could be disconcerting and/or disorienting to the user.

Therefore, in an APPLY STAGED HAPTIC FEEDBACK TRANSITION step 130, a staged transition is performed from the original haptic feedback profile to the desired haptic feedback profile for the new control state. In other words, the transition from the original haptic feedback profile to the desired haptic feedback profile includes at least one intermediate stage that reduces the sudden change in haptic feedback that would occur from an immediate switch between the old and new haptic profiles corresponding to the switch between control states.

Figure 2A:
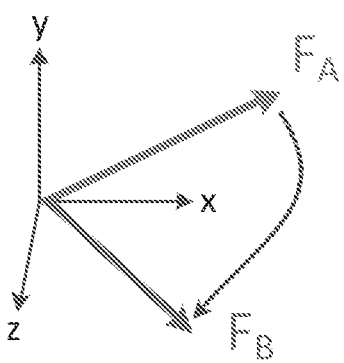
FIG. 2A shows an exemplary haptic force vector transition during a control state change, in accordance with various embodiments of the invention.
Figure 2B:
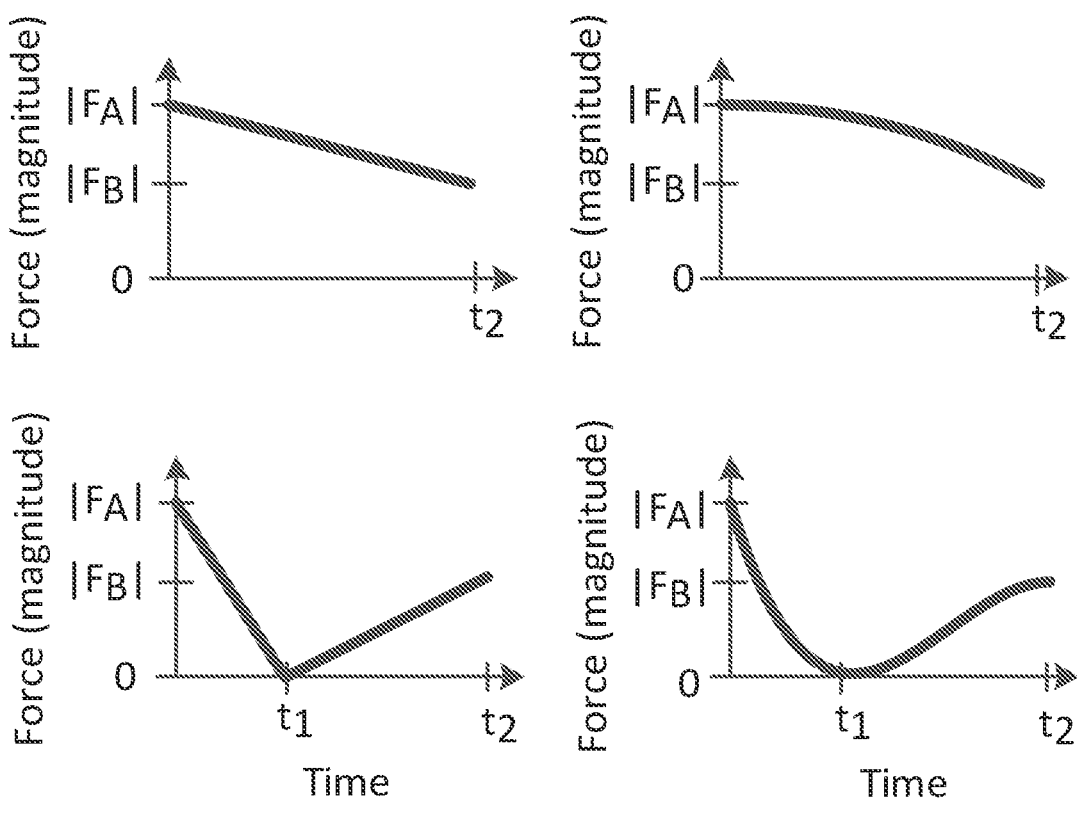
FIG. 2B shows exemplary haptic force feedback transition profiles in accordance with various embodiments of the invention.

Often, this transition from the original haptic feedback profile to the desired (new) haptic feedback profile will involve an adjustment to the force feedback vector expressed at the input device. FIG. 2A shows an exemplary haptic force feedback vector transition from an initial force $F_A$ to a new force $F_B$. Force $F_A$ can be greater than or less than force $F_B$ (or in some embodiments equivalent, where the transition is one of direction only). The staged transition from force $F_A$ to a new force $F_B$ can take any path, including linear or curvilinear transitions, and can include discontinuities (e.g., steps) as part of the transition. For example, FIG. 2B shows several exemplary staged transitions between haptic feedback profiles that could occur in response to step 120, including a straight linear scaling (#1), a monotonic scaling (#2), a sawtooth bidirectional scaling (#3), and a curvilinear multi-directional scaling (#4). In some instances, the transition may move the force magnitude through a zero force state (e.g., #3 and #4). In various other embodiments, the transition from force $F_A$ to force $F_B$ could use several algorithms, including summing scaled versions of forces $F_A$ and $F_B$ to create intermediate direction vectors or remaining aligned with force $F_A$ for a period of time and then with force $F_B$.

Note that in some embodiments, a "phantom" haptic feedback can be maintained when changing between a control state having haptic feedback and a control state that normally would not generate haptic feedback. FIG. 1B shows an exemplary method for providing this type of stable transition.

As described above with respect to FIG. 1A, in a PROVIDE HAPTIC FEEDBACK step 110, the surgical system is in a control state that provides force feedback to the input device based on haptic model input, such as sensed forces at the instrument and/or other system structure, or haptic feedback profiles based on virtual or synthetic interactive elements (e.g., user interface elements, virtual fences, and/or virtual control features, among others). Also as above, the haptic feedback in step 110 may also include forces that are computed based on additional sensors of the surgical system such as position sensors, buttons, or contact sensors. And in a CHANGE CONTROL STATE step 120, the control state of the surgical system changes to a control state for which haptic feedback is not associated (or is different than the original haptic feedback profile), such as a system settings mode, an arm change mode (i.e., switching control to a different instrument on the surgical system), or an exit following mode (i.e., simply disabling the control link between the input device and the surgical instrument), among others.

Then, in a MAINTAIN HAPTIC FEEDBACK step 125, the haptic feedback profile is left unchanged even as the control state of the system changes. Such haptic feedback consistency can sometimes provide a more intuitive experience for the user, compared to changing or eliminating feedback altogether. For example, changing from an instrument control state (having haptic feedback) to a control state in which the input device is used to change system parameters (e.g., selecting menu options) and therefore does not have any logical haptic feedback relationship to the surgical instrument forces, it can be beneficial to simply maintain the feedback profile from the instrument control state even during the system settings control state, so that when the control state changes back to the instrument control state, the user is not surprised by a sudden appearance of force feedback at the input device. Thus, even though the haptic feedback profile in the new state is technically inconsistent with the control actions performed at the input device for the new state, that haptic inconsistency can actually provide a more consistent user experience.

Note that in some embodiments, step 125 can include overlaying or adding additional haptic feedback associated with the new control state to the original haptic feedback profile. For in the system settings example described above, certain haptic feedback effects could be associated with the system settings control state, such as haptic "clicks" or "bumps" when settings are changed or selected. In some embodiments, such haptic effects could be provided along with the original force feedback from the previous control state.

Note further that in some embodiments, the haptic feedback maintenance of step 125 can be followed by an APPLY STAGED HAPTIC FEEDBACK TRANSITION step 130, as described above with respect to FIG. 1A. In such case, the haptic feedback profile would be initially unchanged after the control state change of step 120, but would eventually undergo a staged transition to a new haptic feedback profile.

Figure 3A:
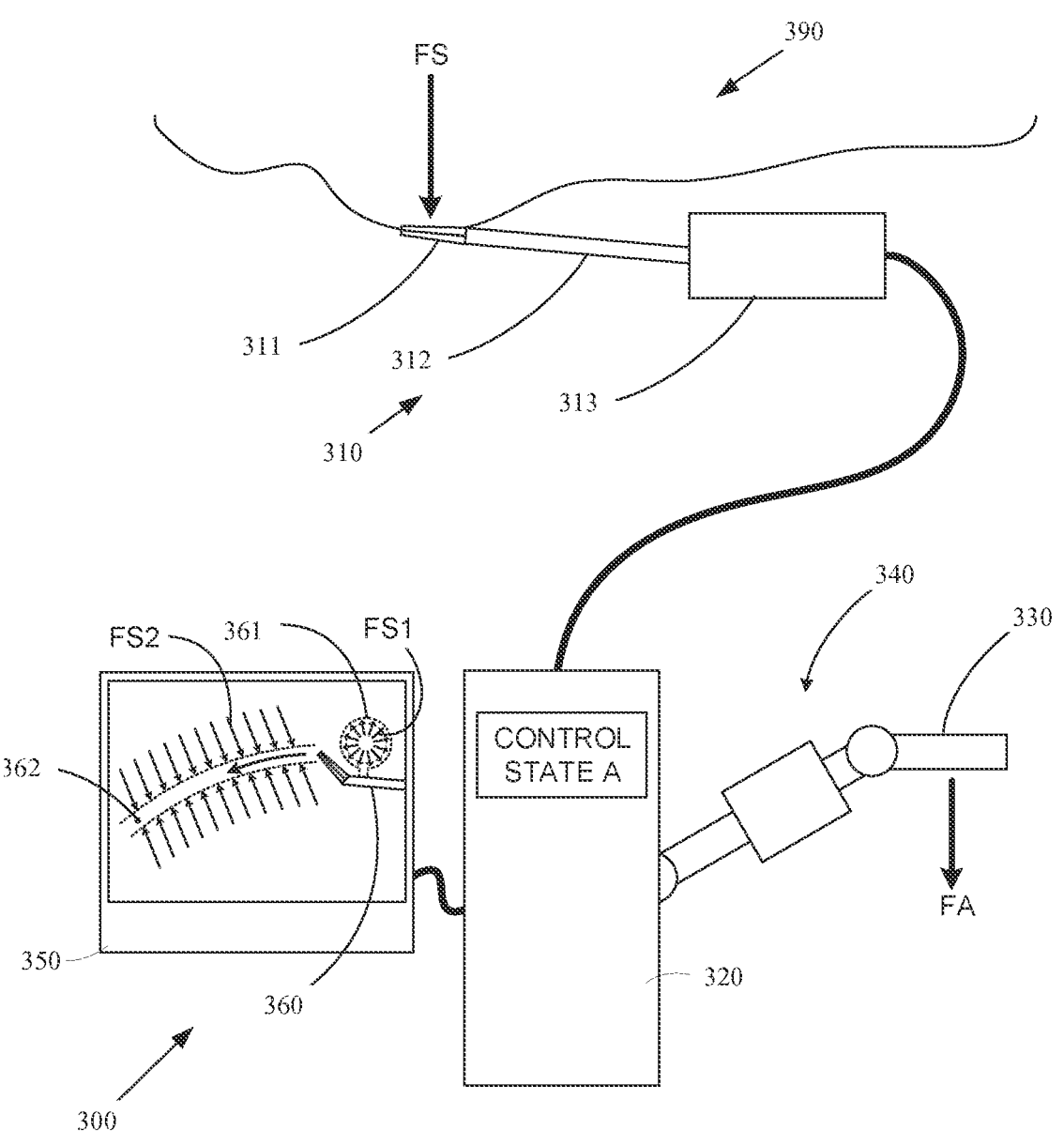
FIGS. 3A-3C show an exemplary surgical system providing a haptic force feedback transition in response to a change in control state, in accordance with various embodiments of the invention.

FIG. 3A shows a block diagram of a surgical system 300 incorporating haptic feedback and means for providing an intuitive haptic experience for the user as described above with respect to FIGS. 1A and/or 1B. Surgical system 300 includes an instrument 310 for performing a surgical task (e.g., forceps, cutter, retractor, vessel sealer, needle driver, catheter, etc.), an input device 330 (e.g., a lever(s), gripper(s), joystick(s), or any other structure capable of receiving user input) for receiving inputs from a user (e.g., surgeon), and a controller 320 for receiving input instructions from input device 330, controlling the actions of instrument 310 accordingly via a manipulation structure 313, and providing instructions to a haptic feedback actuator 340 to provide haptic feedback to input device 330 according to a desired haptic feedback profile. In various embodiments, manipulation structure 313 can include any number of systems and structures for maneuvering, positioning, actuating, or otherwise controlling the behavior of instrument 310, including a robotic arm(s)/manipulator(s), set up structure(s), and/or positioning element(s) such as a boom(s) or cart(s), among others. Controller 320 can include any combination of hardware, software, firmware, and other modalities for generating, managing, controlling, and effecting the actions described herein. In various embodiments, controller 320 can be integrated with instrument 310, input device 330, and/or discrete control hardware (e.g., a standalone processing unit or computing platform).

For exemplary purposes, FIG. 3A shows surgical system 300 in a control state A, in which input device 330 is controlling instrument 310. As depicted in FIG. 3A, the surgeon has used input device 330 to grasp and retract a portion of tissue 390 with an end effector 311 on shaft 312 of instrument 310. This results in a downward force Fs at end effector 311, and in response controller 320 delivers a haptic feedback force FA to input device 330 (e.g., as described with respect to step 110 above). In this manner, the surgeon would "feel" the resistance being provided by tissue 390 as it is being retracted.

Note that this description of control state A is for exemplary purposes only, as this initial control state A could be any state of surgical system 300. For example, while the haptic feedback profile force FA is described as being derived from a force FS sensed at end effector 311 of instrument 310 for exemplary purposes, in various other embodiments, force FS could be sensed at any location for which corresponding haptic feedback at input device 330 would be beneficial, such as interactions at shaft 312 or any other element of manipulation structure 313 (e.g., arm pressure against structures or staff).

In various other embodiments, force FS can be defined according to non-physical parameters, such as the synthetic interactive elements described above. For example, in some embodiments, surgical system 300 can include an optional display 350 (e.g., a monitor(s), a head-in viewer(s), projections, video glasses/helmet(s), and/or any other graphical presentation element). In various embodiments, display 350 can present a virtual or synthetic element 361 that can be interacted with via input device 330. In some embodiments, synthetic element 361 can be used as a supplemental interface for interacting with a physical component of surgical system 300. For example, as shown in FIG. 3A, synthetic element 361 can be a virtual handle or knob that can be "grasped" and dragged around using input device 330 to reposition instrument 310 at the surgical site. In other embodiments, synthetic element 361 can provide a purely virtual interaction element, such as a dial, toggle, lever, or any other structure for controlling surgical system 300. In any case, by generating a haptic feedback profile based on model forces FS1 associated with interacting with synthetic element 361 (e.g., radially outward resistive force produced with grasping a round knob), controller 320 can then attempt to provide an appropriate haptic feedback profile force FA at input device 330.

In various other embodiments, surgical system 300 may provide guidance to the user with respect to movement of instrument 310 and/or input device 330. For example, a desired motion of instrument 310 (e.g., a targeted or safe dissection path, a desired retraction movement, or any other beneficial articulation) could optionally be defined as a trajectory 362. By generating a haptic feedback profile based on model forces FS2 associated with maintaining the position of instrument 310 along trajectory 362 (e.g., inwardly directed forces produced upon deviations from trajectory 362), controller 320 can then attempt to provide an appropriate haptic feedback profile force FA at input device 330.

Figure 3B:
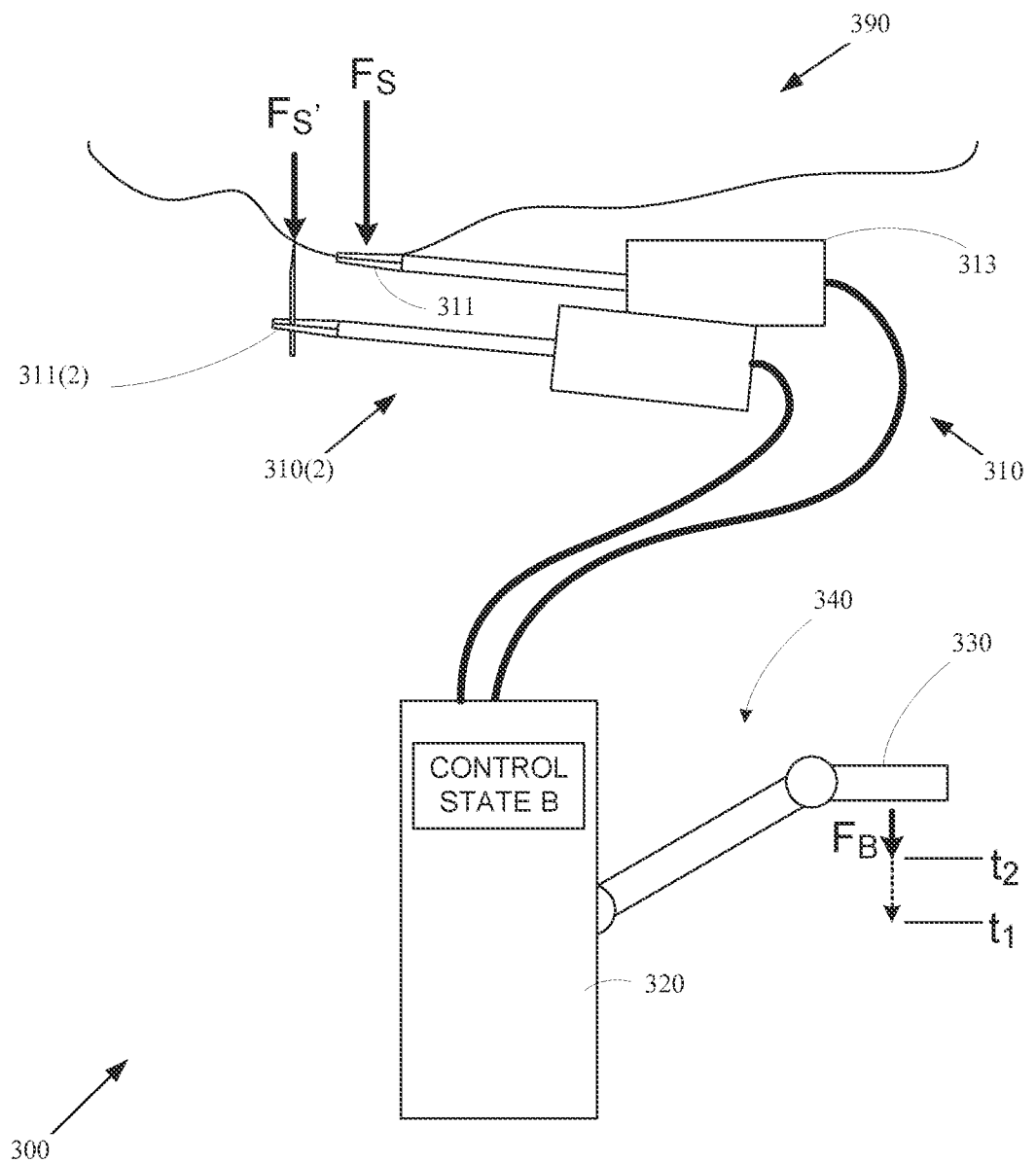

Then, in an exemplary control state change to a new control state B depicted in FIG. 3B (e.g., as described with respect to step 120 above) shifts control by input device 330 from its existing element (e.g., original instrument 310 such as a retractor) to a new element (e.g., instrument 310(2) such as a needle driver for suturing tissue 390). The control state change results in a force Fs' at the new element (e.g., instrument 310(2)), different than the force Fs at original element (e.g., instrument 310), needing to be expressed as haptic feedback $F_B$ at input device 330. Thus, over a time (t2–t1), a staged transition from haptic force feedback $F_A$ to $F_B$ is performed, as described with respect to step 130 above. As noted previously, because of the staged transition the user at input device 330 does not experience a sudden and disconcerting jump from force feedback $F_A$ to $F_B$ that would otherwise occur if the force feedback transformation applied to the sensed force switched concurrently with the control state change. For example, the staged transition would ensure that haptic feedback representative of supporting retracted tissue would not immediately vanish, or that the sense of holding a virtual knob or handle would not immediately disappear.

Figure 3C:
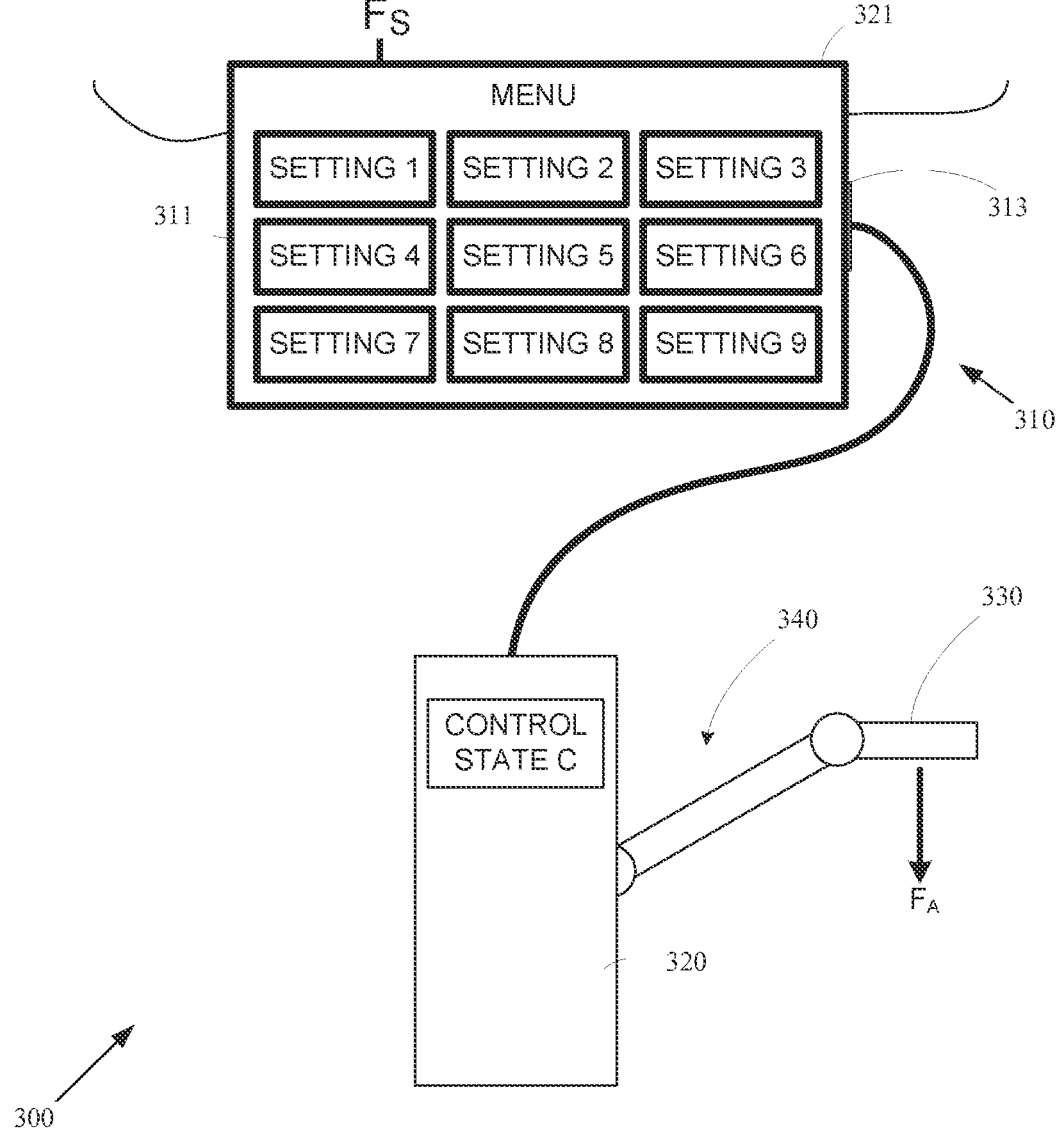

In other embodiments, another exemplary control state change from control state A in FIG. 3A to a new control state C depicted in FIG. 3C (e.g., as described with respect to step 125 above) shifts input device 330 control from instrument 310 (or any other control state with haptic feedback) to a system setting selection interface 321 (or any other control state with no haptic feedback (or different haptic feedback)). Here, the haptic feedback profile is maintained even as the control state is changed, and thus the feedback force at input device 330 is maintained as force $F_A$, even though the settings selection menu is not a force-generating environment. As a result, the user is not surprised by a sudden disappearance of force feedback at the input device (or a sudden reappearance of force feedback once the selection menu is exited).

As noted above, in some embodiments the retained haptic force $F_A$ be overlaid with additional haptic feedback associated with the new control state, such as haptic "clicks" or "bumps" when settings are changed or selected. As further noted above, the maintained haptic feedback can be followed by a subsequent staged transition to a new haptic feedback profile.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A method comprising:
outputting, by a controller during a first control state of a surgical system and at an input device of the surgical system, haptic feedback associated with a first non-zero haptic force feedback profile;
detecting, by the controller, a transition from the first control state to a second control state of the surgical system; and
implementing, by the controller, a phantom non-zero haptic force feedback profile to maintain the first haptic feedback during the second control state.

2. The method of claim 1, wherein:
the phantom non-zero haptic force feedback profile is inconsistent with a user control action performed at the input device in the second control state.

3. The method of claim 2, further comprising:
overlaying at least one haptic effect onto the first non-zero haptic force feedback profile.

4. The method of claim 1, further comprising:
restoring the first non-zero haptic force feedback profile at the input device on a condition in which the surgical system transitions from the second control state to the first control state.

5. The method of claim 1, further comprising:
controlling a surgical instrument according to user input received at the input device while the surgical system is in the first control state;
receiving sensed force data from the surgical instrument during the controlling; and
generating the first non-zero haptic force feedback profile based on the sensed force data.

6. The method of claim 1, wherein:
the first non-zero haptic force feedback profile is based on a synthetic interactive element generated by the controller.

7. A surgical system comprising:
an input device; and
a controller operably coupled to the input device;
wherein the controller is configured to perform a plurality of operations including:
outputting, during a first control state of the surgical system and at the input device, haptic feedback associated with a first non-zero haptic force feedback profile;
detecting a transition from the first control state to a second control state of the surgical system; and
implementing a phantom non-zero haptic force feedback profile to maintain the first haptic feedback during the second control state.

8. The surgical system of claim 7, wherein:
the phantom haptic feedback profile is inconsistent with a control action at the input device associated with the second control state.

9. The surgical system of claim 8, wherein:
the plurality of operations includes overlaying at least one haptic effect onto the first non-zero haptic force feedback profile.

10. The surgical system of claim 7, wherein:
the plurality of operations includes restoring the first non-zero haptic force feedback profile at the input device on a condition in which the surgical system transitions from the second control state to the first control state.

11. The surgical system of claim 7, wherein:
the plurality of operations includes:
controlling a surgical instrument according to input associated with the input device while the surgical system in the first control state,
receiving sensed force data from the surgical instrument during the controlling, and
generating the first non-zero haptic force feedback profile based on the sensed force data.

12. The surgical system of claim 7, wherein:
the first non-zero haptic force feedback profile is based on a synthetic interactive element generated by the controller.

* * * * *